(12) United States Patent
Della Valle et al.

(10) Patent No.: US 12,102,608 B2
(45) Date of Patent: Oct. 1, 2024

(54) COMPOSITION OF ACYLETHANOLAMIDES FROM OLIVE OIL FATTY ACIDS

(71) Applicant: EPITECH GROUP S.P.A., Milan (IT)

(72) Inventors: Francesco Della Valle, Milan (IT); Maria Federica Della Valle, Milan (IT); Gabriele Marcolongo, Milan (IT); Chiara Gomiero, Milan (IT)

(73) Assignee: EPITECH GROUP S.P.A., Milan (IT)

( * ) Notice: Subject to any disclaimer, the term of this patent is extended or adjusted under 35 U.S.C. 154(b) by 78 days.

(21) Appl. No.: 17/825,260

(22) Filed: May 26, 2022

(65) Prior Publication Data

US 2022/0378725 A1 Dec. 1, 2022

(30) Foreign Application Priority Data

May 28, 2021 (IT) .................. 102021000014006

(51) Int. Cl.
*A61K 31/164* (2006.01)
*A23L 33/115* (2016.01)

(52) U.S. Cl.
CPC .......... *A61K 31/164* (2013.01); *A23L 33/115* (2016.08)

(58) Field of Classification Search
CPC .......................... A61K 31/164; A23L 33/115
See application file for complete search history.

(56) References Cited

U.S. PATENT DOCUMENTS

2019/0365675 A1* 12/2019 Orío Ortiz ............. A61K 31/64

FOREIGN PATENT DOCUMENTS

| WO | WO-2008023998 A1 * | 2/2008 | ............. A61K 31/16 |
|----|---------------------|--------|-------------------------|
| WO | 2019/066644 A1 | 4/2019 | |

OTHER PUBLICATIONS

Tsuboi, et al. Endocannabinoids and related N-acylethanolamines : biological activities and metabolism, Inflammation and Regeneration, 38, p. 1-10. (Year: 2018).*
Salvemini, D et al., "Nitric oxide: a key mediator in the early and late phase of carrageenan-induced rat paw Inflammation", British Journal of Pharmacology, 118: 829-838 (1996).
Italian Search Report for Italian Patent Application No. 102021000014006 mailed Feb. 15, 2022, 10 pages.
Borrelli, F. et al., "Role of acylethanolamides in the gastrointestinal tract with special reference to food intake and energy balance", Best Practive & Research Clinical Endcrinology & Metabolism, 23(1): 33-49 (Feb. 2009).
Martin-Sanchez, A. et al., "Alcohol-induced conditioned place preference is modulated by CB2 cannabinoid receptors and modifies levels of endocannabinoids in the mesocorticolimbic system", Pharmacology Biochemistry and Behavoir, 183: 22-31 (2019).
Wang, X. et al., "Scalable synthesis of oleoyl ethanolamide by chemical amidation in a mixed solvernt", Journal of the American Oil Chemists Society, 93(1): 125-131 (Nov. 2015).
Wu, J. et al., "Oxylipins, endocannabinoids, and related compounds in human milk: Levels and effects of storage conditions", Prostaglandins and Other Lipid Mediators, 122: 28-36 (Dec. 2015).

\* cited by examiner

*Primary Examiner* — Matthew P Coughlin
*Assistant Examiner* — Meghan C Heasley
(74) *Attorney, Agent, or Firm* — Merchant & Gould P.C.

(57) ABSTRACT

A composition of acylethanolamides is obtained from olive oil fatty acids and is used in treating neuroinflammation. The acylethanolamide complex includes (weight percentages):

| | |
|---|---|
| oleoylethanolamide (OEA) C18:1 | 60-65% |
| palmitoylethanolamide (PEA) C16:0 | 5-20% |
| linoleylethanolamide (LEA) C18:2 | 5-20% |
| stearoylethanolamide (SEA) C18:0 | 1-2% |
| palmitoylethanolamide (POEA) C16:1 | 0.1-0.8% |
| myristoylethanolamide (MEA) C14:0 | 0.02-0.15% |
| mixture of glycerides | 4-6% |
| glycerol | 6-8%. |

A method obtains the acylethanolamide complex and formulations contain the acylethanolamide complex.

19 Claims, 2 Drawing Sheets

COMPOSITION OF ACYLETHANOLAMIDES FROM OLIVE OIL FATTY ACIDS

This application claims benefit of Serial No. 102021000014006, filed 28 May 2021 in Italy and which application is incorporated herein by reference. To the extent appropriate, a claim of priority is made to the above disclosed application.

TECHNICAL FIELD OF THE INVENTION

The present invention relates to a composition of acylethanolamides obtained from olive oil fatty acids and the use thereof in treating neuroinflammation.

BACKGROUND ART

One of the most common pathological conditions associated with low-grade neuroinflammation in both humans and animals is obesity. Obesity is a chronic pathological condition characterized by the excessive and abnormal deposit of fat (World Health Organization, 2017) which affects humans but pets as well: in fact, to date it is the most common nutritional disease in dogs with an incidence varying between 24% and 44% of animals subjected to veterinary controls.

Several experimental evidence has shown that obesity is characterized by a state of chronic low-grade inflammation caused by the production of different inflammation mediators. In this pathological condition, it is currently established that mast cells actively participate in the appearance and maintenance of chronic low-grade inflammation in adipose tissue by releasing chemokines (CCL2, CXCL8), cytokines (IL-6, IL-8 and TNF-a) which together with pro-inflammatory adipocytokines (leptin, adiponectin and other molecules) released from the adipose tissue itself, induce and maintain a permanent neuroinflammatory state which tends not to resolve. Such a neuroinflammatory state is considered to be responsible for the development of several chronic and/or degenerative diseases such as, inter alia, osteoarthritis, rheumatoid arthritis, cardiovascular diseases, inflammatory bowel diseases, Alzheimer's and vascular dementia in both humans and animals.

In obesity, the overproduction of adipocytokines negatively influences multiple functions such as appetite and energy balance, insulin sensitivity/resistance, recruitment of immune cells in adipose tissue and angiogenesis while the massive release of cytokines by the degranulating mast cells amplifies the neuroinflammatory process.

To date, an effective treatment for weight loss is the association between a balanced diet and physical activity: however, although useful for the weight loss of man and animal, this protocol is not able to attenuate, to the point of "extinguishing", chronic low-grade inflammation caused mainly by excessive and unregulated mast cell degranulation.

It is thus of fundamental importance to have molecules available with anti-neuroinflammatory properties capable of sub-modulating the production of pro-neuroinflammatory factors released by the activated mast cells.

Although palmitoylethanolamide is a molecule known for the activity thereof in regulating mast cell degranulation, it has proved to be substantially ineffective on this type of neuroinflammatory manifestation, if not at rather high doses.

SUMMARY OF THE INVENTION

The present invention comes from the surprising discovery that a composition obtained by direct aminolysis of the fatty acids contained in olive oil is capable of determining a clear synergy of the acylethanolamide molecules (particularly OEA and PEA) with respect to the corresponding pure acylamides, in counteracting neuro-inflammatory phenomena mediated by the hyper-reactivity of the mast cells and thus by the increase thereof at the tissue level. Such an activity can be particularly related to the neuroinflammatory phenomena being detectable in a population of subjects suffering from obesity.

Therefore, the present invention relates to an acylethanolamide composition as defined below, comprising (weight percentages):

| | |
|---|---|
| oleoylethanolamide (OEA) C18:1 | 60-65% |
| palmitoylethanolamide (PEA) C16:0 | 5-20% |
| linoleylethanolamide (LEA) C18:2 | 5-20% |
| stearoylethanolamide (SEA) C18:0 | 1-2% |
| palmitoleoylethanolamide (POEA) C16:1 | 0.1-0.8% |
| myristoylethanolamide (MEA) C14:0 | 0.02-0.15% |
| mixture of glycerides | 4-6% le |
| glycerol | 6-8%. |

The invention further relates to a direct uncatalyzed aminolysis method in the absence of solvent from olive oil with 2-aminoethanol, comprising the following steps:
  a) mixing olive oil with 2-aminoethanol;
  b) heating the mixture of step a) to a temperature between 120° C. and 160° C.;
  c) separating an acylethanolamide composition thus obtained in the form of a waxy solid;
  d) optionally, absorbing the acylethanolamide composition of step c) on porous amorphous silica, thus obtaining an acylethanolamide composition/porous amorphous silica adsorption compound.

Therefore, the present invention also relates to an acylethanolamide composition as defined below for use in treating low-grade neuroinflammation, in particular in patients suffering from obesity, i.e., the use of said acylethanolamide composition for the preparation of a medicament for treating such diseases.

These and further objects, as outlined in the appended claims, will be described in the following description. The text of the claims should be considered included in the description in order to assess the description sufficiency.

Further features and advantages of the invention will become apparent from the following description of preferred embodiments, given by way of non-limiting examples.

DETAILED DESCRIPTION OF THE INVENTION

Figure 1:
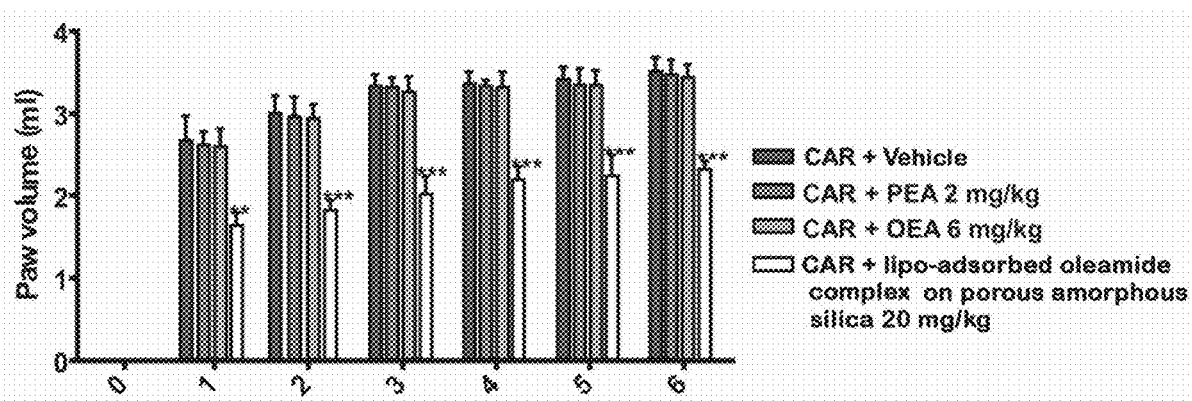
FIG. 1 shows a graph of the increase in the volume of the treated animal's paw vs. time measurements after treatment; the values shown in the graph represent the average ± SEM. One-Way ANOVA test: $p<0.01$ vs. CAR, *$p<0.001$ vs. CAR.

In a first aspect, the present invention relates to an acylethanolamide composition comprising (weight percentages):

| | |
|---|---|
| oleoylethanolamide (OEA) C18:1 | 60-65% |
| palmitoylethanolamide (PEA) C16:0 | 5-20% |
| linoleylethanolamide (LEA) C18:2 | 5-20% |
| stearoylethanolamide (SEA) C18:0 | 1-2% |
| palmitoleoylethanolamide (POEA) C16:1 | 0.1-0.8% |
| myristoylethanolamide (MEA) C14:0 | 0.02-0.15% |
| mixture of glycerides | 4-6% |
| glycerol | 6-8%. |

The composition of the invention, although characterized by an OEA content higher than or equal to 60% by weight, may have a variability of the PEA and LEA content depending on the origin of the olive oil or the variety of the plant from which it originates.

Preferably, in an embodiment the composition of the invention comprises (weight percentages):

| | |
|---|---|
| oleoylethanolamide (OEA) C18:1 | 61-63% |
| palmitoylethanolamide (PEA) C16:0 | 17-19% |
| linoleylethanolamide (LEA) C18:2 | 5-5.7% |
| stearoylethanolamide (SEA) C18:0 | 1.2-1.7% |
| palmitoleoylethanolamide (POEA) C16:1 | 0.3-0.5% |
| myristoylethanolamide (MEA) C14:0 | 0.03-0.11% |
| mixture of glycerides | 5-5.5% |
| glycerol | 7-7.5%. |

In a different embodiment, the composition of the invention comprises (weight percentages):

| | |
|---|---|
| oleoylethanolamide (OEA) C18:1 | 61-63% |
| palmitoylethanolamide (PEA) C16:0 | 7-12% |
| linoleylethanolamide (LEA) C18:2 | 8-15% |
| stearoylethanolamide (SEA) C18:0 | 1.2-1.7% |
| palmitoleoylethanolamide (POEA) C16:1 | 0.3-0.5% |
| myristoylethanolamide (MEA) C14:0 | 0.03-0.11% |
| mixture of glycerides | 5-5.5% |
| glycerol | 7-7.5%. |

The composition according to the invention, containing the aforesaid components, will also be referred to as an "acylethanolamide complex" below for brevity, in which the term "acylethanolamide complex", as used for the purposes of the present invention, means a set of components in which acylethanolamides form the predominant part of the composition.

The composition according to the invention can be obtained from olive oil by direct uncatalyzed aminolysis in the absence of solvent with 2-aminoethanol.

More in particular, the method according to the invention comprises the following steps:
a) mixing olive oil with 2-aminoethanol;
b) heating the mixture of step a) to a temperature between 120° C. and 160° C.;
c) separating the acylethanolamide composition or complex of the invention in the form of a waxy solid;
d) optionally, absorbing the acylethanolamide composition or complex of step c) on porous amorphous silica, thus obtaining an acylethanolamide composition/porous amorphous silica adsorption compound.

The composition of the invention may vary, in particular as for the PEA and LEA content, depending on the olive oil used.

Below are the typical average compositions of olive oil from olive growing in European Union countries (olive oil A) and olive oil from olive growing in Italy (olive oil B).

Olive oil A—Composition range in the main fatty acids of Olive Oil (EC Reg 1989/03):

| | |
|---|---|
| Myristic acid (C14:0) | <0.1% |
| Palmitic acid (C16:0) | 7.5-20% |
| Palmitoleic acid (C16:1) | 0.3-3.5% |
| Stearic acid (C18:0) | 0.5-5.0% |
| Oleic acid (C18:1) | 55-83% |
| Linoleic acid (C18:2) | 2.5-21% |

Olive oil B—Typical Composition (Average of 1050 Samples) in the Main Fatty Acids of Italian Olive Oil (Italian National Database of Monovarietal Extra Virgin Olive Oil-2013 DOI: 10.5772/51772):

| | |
|---|---|
| Myristic acid (C14:0) | <0.1% |
| Palmitic acid (C16:0) | 12% |
| Palmitoleic acid (C16:1) | 1.1% |
| Stearic acid (C18:0) | 2.2% |
| Oleic acid (C18:1) | 73% |
| Linoleic acid (C18:2) | 10.3%. |

Step a) is preferably carried out at room temperature. The weight ratio of olive oil to 2-ethanolamine is preferably between 100:13 and 100:22, more preferably between 100:15 and 100:20, even more preferably between 100:16 and 100:18. The amount of 2-aminoethanol used is thus lower than the stoichiometric in order to succeed in maintaining in the semi-synthesis product, together with the glycerol released in the reaction, also a portion of monoglycerides useful for improving the bioavailability of the acylethanolamide complex formed.

Preferably, step a) is carried out in an inert gas atmosphere, for example under nitrogen.

Step b) is preferably carried out at a temperature between 130° C. and 150° C., more preferably between 135° C. and 145° C. and preferably for a time over 2 hours, more preferably over 3 hours and less than 5 hours.

Step c) is preferably carried out by slow cooling to room temperature.

Step d) is preferably carried out by melting the acylethanolamide complex of step c) at a temperature between 70° C. and 90° C. and then adding porous amorphous silica. The acylethanolamide complex/porous amorphous silica weight ratio is preferably between 0.9:1 and 1.1:1, more preferably is about 1:1.

As will be better illustrated by the biological experiments and related graphs below, the acylethanolamide composition according to the invention has demonstrated, in animal models of neuroinflammation and in tissue evaluations, a significant synergistic effect as compared to the administration of the individual compounds PEA and OEA (which form the predominant part of the composition) administered at the same dosage. Such a synergistic effect can be related to the combination in a single composition of PEA and OEA, but also to the presence in the same composition of other acylethanolamides, as well as a not insignificant amount of fatty acid monoglycerides which improve the bioavailability of the composition.

Therefore, the invention further relates to the acylethanolamide composition, as such or in the form of an acylethanolamide composition/porous amorphous silica adsorption compound, for use in the treatment of low grade neuroinflammation, preferably in a population of patients suffering from obesity.

CHEMICAL EXAMPLE (SEMI-SYNTHESIS)

Preparation of the Acylethanolamide Composition (Acylethanolamide Complex)

295.0 g of Olive Oil from olive trees grown in European Union countries are placed in a glass flask provided with stirring and a reflux refrigerant. A nitrogen saturation is activated so as to eliminate the oxygen during the semi-synthesis. 55.0 g of 2-aminoethanol are added at room temperature and under stirring, then the temperature is slowly raised (in about 1 hour) to 140° C. with an oil bath; the amount of 2-aminoethanol used is less than the stoichiometric in order to succeed in maintaining in the semi-synthesis product, together with the glycerol which is released in the reaction, also a portion of monoglycerides useful for improving the bioavailability of the acylethanolamide complex which is formed. The heating is maintained for 4 hours always under nitrogen flow. The semi-synthesis mixture is then cooled slowly (room temperature reached in about 1 hour); a yellowish solid of waxy consistency is obtained. The composition of the solid obtained (average of 5 semi-syntheses) is shown in Table 1 below:

TABLE 1 weight composition of the acylethanolamide complex

| | |
|---|---|
| Oleoylethanolamide (C18:1) OEA | 62.2% |
| Palmitoylethanolamide (C16:0) PEA | 18.3% |
| Linoleylethanolamide (C18:2) LEA | 5.4% |
| Stearoylethanolamide (C18:0) SEA | 1.5% |
| Palmitoleoylethanolamide (C16:1) POEA | 0.4% |
| Myristoylethanolamide (C14:0) MEA | ≤0.1% |
| Mixture of glycerides | 5.2% |
| Glycerol | 7.3% |

The acylethanolamide complex thus obtained can be used directly for the preparation of liquid forms for oral use, through suitable emulsification processes; alternatively it can be subjected to lipo-adsorption on silica as indicated below.

Lipo-adsorption of Acylethanolamide Complex on Silica 100 g of acylethanolamide complex from the semi-synthesis are melted at 80° C. in a nitrogen flow; after melting, 100 g of porous amorphous silica (Syloid XDP-Grace) are slowly added under stirring. After intense and prolonged stirring, the obtained mass is slowly cooled to room temperature. A homogeneous and flowing powder is obtained which can be easily used for the preparation of solid pharmaceutical forms for oral use.

BIOLOGICAL EXAMPLE

The study was conducted on male Sprague-Dawley rats (200-235 g; Harlan, Nossan, Italy) fed ad libitum and housed in cages with a controlled sleep/wake cycle. Before the start of the experimentation, the animals were subjected to an acclimatization period of 1 week considering all the experimental procedures and protocols, compliant with the principles of the care of laboratory animals approved by the Italian Ministry of Health and respecting the guidelines of the European Economic Community.

The animals were subjected to a single injection of 100 µl of saline solution containing 1% Carrageenan (CAR) in one of the two hind legs. Paw edema was measured with a plethysmometer (Ugo Basile, Comerio, Varese, Italy) (Salvemini D et al. *Nitric oxide: A key mediator in the early and late phase of carrageenan-induced rat paw inflammation. Br. J. Pharmacol.* 1996; 118: 829-838) before the CAR injection and after the inoculation thereof every hour for 6 h. The hyperalgesic responses to heat were assessed using the plantar test with a cut-off latency of 20 sec to avoid tissue damage. The rats were individually housed in plexiglass compartments to acclimatize them before subjecting them to thermal stimulation. The suspension latency period of the injected paw was determined by an electronic circuit and the results were expressed in seconds.

Edema was expressed as increased paw volume (mL) after the CAR injection with respect to the pre-injection value for all the animals.

The animals were randomized into 5 groups of 10 animals each:

Group 1: rats not injected with CAR in the hind paw and treated per os with saline solution (sham).

Group 2: rats subjected to a single CAR injection in the hind paw and treated per os 30 minutes before the CAR injection with 2% carboxymethylcellulose (CMC), vehicle used to suspend the molecules to be tested (CAR+vehicle).

Group 3: rats subjected to a single CAR injection in the hind paw and treated per os 30 minutes before the CAR injection, with native PEA (2 mg/kg) suspended in 2% CMC (CAR+PEA 2 mg/kg).

Group 4: rats subjected to a single CAR injection in the hind paw and treated per os 30 minutes before the CAR injection, with OEA (6 mg/kg) suspended in 2% CMC (CAR+OEA 6 mg/kg).

Group 5: rats subjected to a single CAR injection in the hind paw and treated per os 30 minutes before the CAR injection, with acylethanolamide composition/porous amorphous silica adsorption compound at 20 mg/kg suspended in 2% CMC (CAR+acylethanolamide complex/porous amorphous silica 20 mg/kg corresponding to 10 mg/kg acylethanolamide complex).

It should be noted that the weight amount of PEA and OEA in the acylethanolamide complex tested was about 6 mg and 2 mg per 10 mg of acylethanolamide complex, respectively, thus the same dosages used for the individual compounds.

The animals were euthanized 6 h after the CAR injection. The paw tissue was taken, immediately fixed with 10% formaldehyde in saline solution at room temperature for 24 h and subjected to histological staining with Hematoxylin/Eosin (E/E). The morphology of the sections was examined with Axiovision Zeiss microscope (Milan, Italy) and several severity scores of tissue damage were assigned: 0=no inflammation; 1=mild inflammation; 2=mild/moderate inflammation; 3=moderate inflammation; 4=moderate/severe inflammation; 5=severe inflammation.

To assess the presence of mast cells, the tissue sections were stained with Toluidine Blue.

RESULTS

1. The Lipo-Absorbed Acylethanolamide Complex on Porous Amorphous Silica 20 mg/kg Reduces Paw Edema of Animals Injected with CAR.

The CAR injection in the hind paw of the experimental animals causes a significant time-dependent increase in the volume of the animal's hind paw (FIG. 1). The edema caused by CAR is significantly reduced only by the treatment with acylethanolamide complex/porous amorphous silica 20 mg/kg (white column on the right) already 1 h after CAR injection and in the subsequent time measurements analyzed until the end of the experiment time (6 h). No significant reduction in the edema was observed in the untreated group and in the groups of rats treated with only PEA 2 mg/kg and with only OEA 6 mg/kg.

2. The Lipo-Adsorbed Acylethanolamide Complex on Porous Amorphous Silica 20 mg/kg is Capable of Significantly Reducing Thermal Hyperalgesia.

Figure 2:
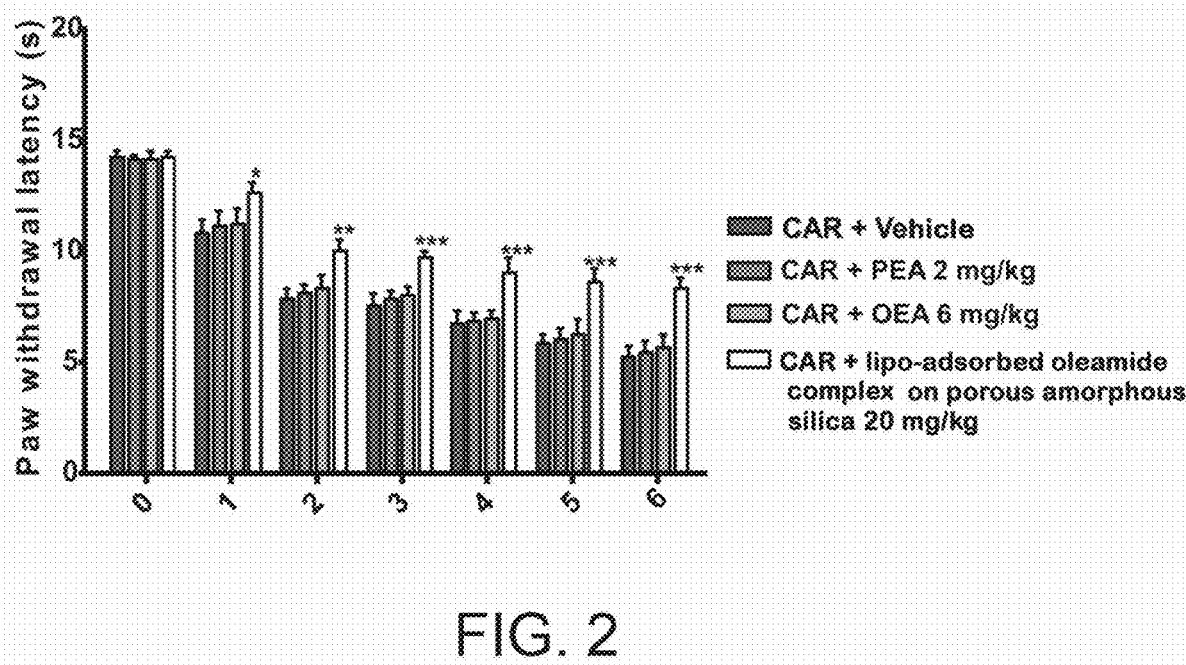
FIG. 2 shows a graph of the retention time (Plantar Test) of the treated animal's paw vs. time measurements after treatment; the values shown in the graph represent the average ± SEM. One-Way ANOVA test: *$p<0.05$ vs. CAR, $p<0.01$ vs. CAR, *$p<0.001$ vs. CAR.

Intraplantar CAR injection induces a time-dependent thermal hyperalgesia maintained until the end of the experiment (6 h). Only the oral administration of the acylethanolamide complex/porous amorphous silica 20 mg/kg (white column on the right) is capable of significantly counteracting the development of CAR-induced thermal hyperalgesia already 1 h after injection and in all the time measurements with respect to the group treated with the vehicle (FIG. 2). No analgesic effect was found in the groups of animals treated with only PEA 2 mg/kg and with only OEA 6 mg/kg.

3. The Lipo-Adsorbed Acylethanolamide Complex on Porous Amorphous Silica 20 mg/kg is Capable of Protecting and Significantly Reducing the Tissue Damage of the Paw of Animals Subjected to CAR Injection.

Figure 3:
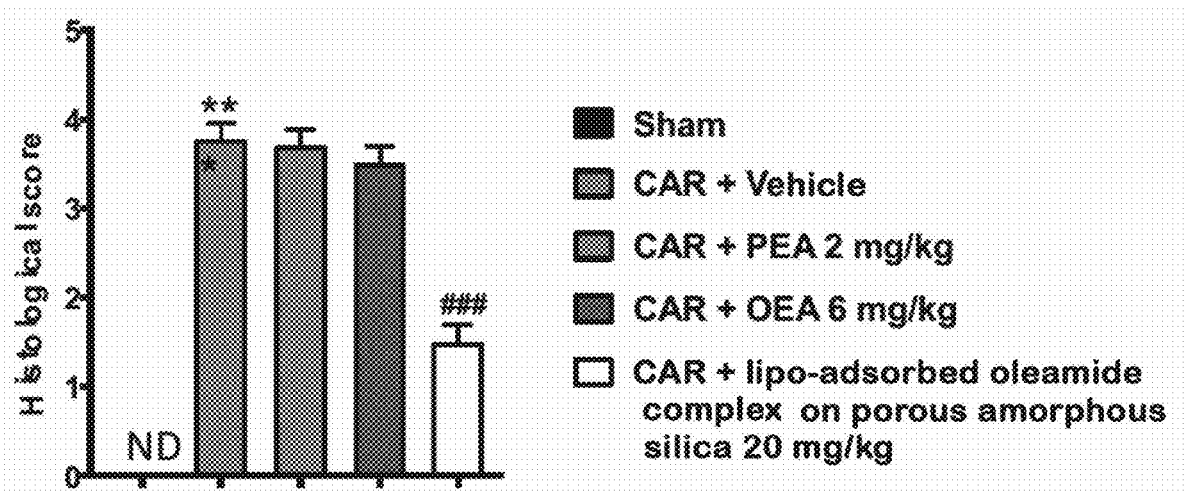
FIG. 3 shows a summary graph of histological analyses performed with E/E; ND=not detectable, from left to right, respectively, CAR-vehicle, CAR+PEA 2 mg/Kg, CAR+ OEA 6 mg/Kg, CAR+acylethanolamide complex/porous amorphous silica; the values shown in the graph represent the average ± SEM. One-Way ANOVA test: ***$p<0.001$ vs. sham, ###$p<0.001$ vs. CAR.

To histologically assess the anti-neuroinflammatory effects of the acylethanolamide complex/porous amorphous silica, the paw tissues of each experimental group were subjected to E/E staining. The results are summarized as scores in FIG. 3. As expected, no tissue damage was found in the sham rats. Conversely, the injection of CAR into the animal's paw causes an evident increase in tissue damage with respect to the healthy animal group. The tissue disruption is significantly reduced by the treatment with acylethanolamide complex/porous amorphous silica 20 mg/kg (white column on the right) while the single molecules of only PEA 2 mg/kg and only OEA 6 mg/kg are not capable of protecting the paw tissues from the neuroinflammatory action of the CAR.

4. The Lipo-Adsorbed Acylethanolamide Complex on Porous Amorphous Silica 20 mg/kg is Capable of Significantly Reducing the Number of Mast Cells in the Paw Tissue of Animals Subjected to CAR Injection.

Figure 4:
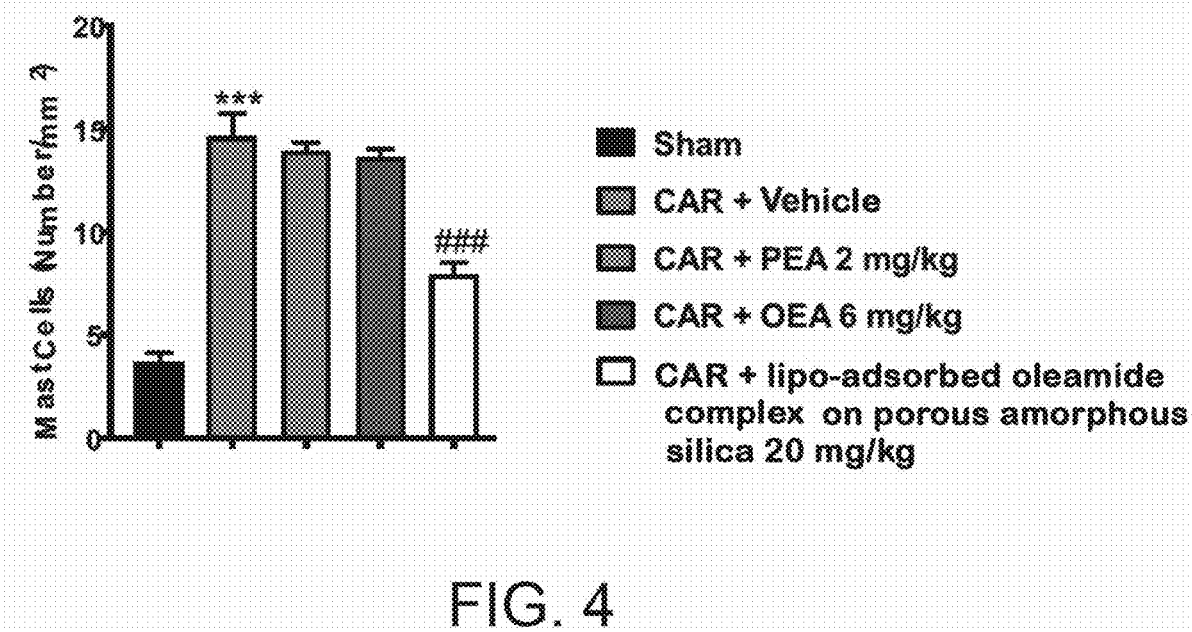
FIG. 4 shows a summary graph (presented as a score) of a tissue mast cell analysis; the values shown in the graph represent the average ± SEM. One-Way ANOVA test: ***p<0.001 vs. sham, ###p<0.001 vs. CAR.

The staining with Toluidine Blue highlights the presence of mast cells in the paw tissue 6 hours after the enema induction. Specifically, the rats injected with CAR and treated with vehicle, with only PEA 2 mg/kg and with only OEA 6 mg/kg show a significant increase in the number of mast cells with respect to the sham group. In contrast, the mast cell infiltrate is significantly reduced only by treatment with the acylethanolamide complex/porous amorphous silica 20 mg/kg. The graph in FIG. 4 summarizes the data (in the form of scores) obtained from the staining with Toluidine Blue.

This data confirms the efficacy of the acylethanolamide complex on a population of patients suffering from obesity, a disease in which an increase in mast cell degranulation occurs.

Moreover, the invention further relates to a formulation comprising the composition (acylethanolamide complex) of the invention or the acylethanolamide composition/porous amorphous silica adsorption compound, in which the formulation is in dosage forms for oral, buccal, parenteral, rectal or transdermal administration.

In particular, the acylethanolamide composition as such will preferably be in the form of an emulsion in liquid dosage forms; conversely, the acylethanolamide composition/porous amorphous silica adsorption compound can preferably be formulated in solid dosage forms.

For oral administration, the pharmaceutical compositions can be found, for example, in the form of tablets or hard or soft capsules, prepared in the conventional manner with pharmaceutically acceptable excipients such as binding agents (e.g., pregelatinized cornstarch, polyvinylpyrrolidone or methylcellulose hydroxypropyl); filling agents (e.g., lactose, microcrystalline cellulose or calcium hydrogen phosphate); lubricants (e.g., magnesium stearate, talc or silica); disintegrants (e.g., potato starch or sodium starch glycolate); or inhibiting agents (e.g. sodium lauryl sulfate). The tablets can be coated through methods well known in the art. The liquid preparations for oral administration can be, for example, in the form of solutions, syrups or suspensions or they can be freeze-dried products to be reconstituted, before use, with water or other suitable vehicles. Such liquid preparations can be prepared through conventional methods with pharmaceutically acceptable additives such as suspending agents (e.g. sorbitol syrup, cellulose derivatives or edible hydrogenated fats); emulsifying agents (e.g. lecithin or acacia); non-aqueous vehicles (e.g. almond oil, oily esters, ethyl alcohol or fractionated vegetable oils); and preservatives (e.g. methyl- or propyl-p-hydroxybenzoates or sorbic acid). The preparation can also conveniently contain flavorings, dyes, and sweetening agents.

The preparations for oral administration can be formulated appropriately to allow the controlled release of the active constituent.

For buccal administration, the compositions can be in the form of tablets or pills formulated in the conventional manner, adapted to an absorption at the level of the buccal mucosa. Typical buccal formulations are tablets for sublingual administration.

The acylethanolamide complex of the invention can be formulated for parenteral administration by injection. The injection formulations can be presented as a single dose, for example in vials, with an added preservative. The compositions can appear in this form as suspensions, solutions, or emulsions in oily or aqueous vehicles and can contain agents of the formulation such as suspension, stabilizing and/or dispersing agents. Alternatively, the active constituent can be found in the form of a powder to be reconstituted, before use, with a suitable vehicle, for example with sterile water.

According to the present invention, the acylethanolamide complex can also be formulated according to rectal compositions such as suppositories or retention enemas, for example containing the base components of the common suppositories such as cocoa butter or other glycerides.

In addition to the compositions described above, the acylethanolamide complex can also be formulated as a deposit preparation. Such long-acting formulations can be administered by implantation (e.g., subcutaneously, transcutaneously or intramuscularly) or intramuscular injection. For example, it can be formulated with appropriate polymer or hydrophobic materials (for example in the form of an emulsion in a suitable oil) or ion exchange resins or as minimally soluble derivatives.

According to the present invention, the dose of acylethanolamide complex suggested for administration to a human (with a body weight of about 70 Kg) is from 1 mg to 2 g or from 10 mg to 700 mg of the active ingredient per unit dose. The dose unit can be administered, for example, 1 to 4 times a day. The dose will depend on the route chosen for administration. It should be considered that it may be necessary to continuously vary the dosage depending on the age and weight of the patient and also on the severity of the clinical condition to be treated. The exact dose and route of administration will ultimately be at the discretion of the attending physician or veterinarian.

The invention further relates to dietary compositions, food supplements, foods for special medical purposes (FSMP) and cosmetic compositions (e.g., in the form of cream) comprising the acylethanolamide complex of the invention.

"Foods for special medical purposes" mean products authorized according to the European Commission Directive to Member States no. 1999/21/EC and following. Such a term refers to a product "intended to meet particular nutritional needs of people affected by a specific disease, disorder or medical condition" in order to cure or help cure the specific medical condition, thus assimilating this FSMP product to a drug.

The formulations according to the invention can be prepared according to conventional methods, such as those described in Remington's Pharmaceutical Sciences Handbook, Mack Pub. Co., N.Y., USA, 17th edition, 1985.

The invention will now be further described through the following formulation examples.

FORMULATION EXAMPLES

Example 1. Liquid Suspension for Oral Use per 100 ml:

| | |
|---|---|
| Acylethanolamide (complex) composition | 12.0 g |
| Corn dextrin | 3 0 g |
| Microcrystalline cellulose | 1.35 g |
| Carboxymethyl cellulose | 0.65 g |
| Polysorbate 80 | 0.10 g |
| Benzoic Acid | 0.08 g |
| Potassium Sorbate | 0.10 g |
| Citric acid | 0.05 g |
| Water | 67.7 g |

Example 2. Tablet per 1 Tablet:

| | |
|---|---|
| Acylethanolamide (complex) composition/porous amorphous silica | 600 mg |
| Microcrystalline cellulose | 250 mg |
| Cross-linked sodium carboxymethyl cellulose | 80 mg |
| Hydroxypropyl cellulose | 20 mg |
| Polysorbate 80 | 5 mg |
| Magnesium Stearate | 6 mg |
| Silicon dioxide | 10 mg |

Example 3. Tablet for Veterinary Use per 1 Tablet:

| | |
|---|---|
| Acylethanolamide (complex) composition/porous amorphous silica | 600 mg |
| Palatability enhancer F20729 | 85 mg |
| Microcrystalline cellulose | 140 mg |
| Cross-linked sodium carboxymethyl cellulose | 54 mg |
| Glyceryl Dibehenate | 90 mg |
| Hydroxypropyl cellulose | 20 mg |
| Polysorbate 80 | 5 mg |
| Magnesium Stearate | 6 mg |

Example 4. Rigid Gelatin Capsule

| | |
|---|---|
| Vegetable gelatin capsule (acid-resistant) | per 1 capsule: |
| Acylethanolamide (complex) composition/porous amorphous silica | 360 mg |
| Glyceryl Dibehenate | 40 mg |

Example 5. Effervescent Tablet per 1 Tablet:

| | |
|---|---|
| Acylethanolamide (complex) composition/porous amorphous silica | 400 mg |
| Potassium bicarbonate | 343 mg |
| Potassium carbonate | 108 mg |
| Anhydrous citric acid | 384 mg |
| Fructose | 130 mg |
| Polysorbate 80 | 15 mg |
| Lemon flavoring | 10 mg |

Example 6. Oro-Soluble Granules 1 g Granules:

| | |
|---|---|
| Acylethanolamide (complex) composition | 600 mg |
| Fructose | 230 mg |
| Sorbitol | 90 mg |
| Anhydrous citric acid | 20 mg |
| Sucrose palmitic ester | 18 mg |
| Polysorbate 80 | 5 mg |
| Polyvinylpyrrolidone 30 | 15 mg |
| Cross-linked sodium carboxymethyl cellulose | 12 mg |
| Flavoring | 10 mg. |

The invention claimed is:

1. An acylethanolamide composition comprising (percentages by weight):

| | |
|---|---|
| oleoylethanolamide (OEA) C18:1 | 60-65% |
| palmitoylethanolamide (PEA) C16:0 | 5-20% |
| linoleylethanolamide (LEA) C18:2 | 5-20% |
| stearoylethanolamide (SEA) C18:0 | 1-2% |
| palmitoleoylethanolamide (POEA) C16:1 | 0.1-0.8% |
| myristoylethanolamide (MEA) C14:0 | 0.02-0.15% |
| mixture of glycerides | 4-6% |
| glycerol | 6-8%. |

2. The acylethanolamide composition according to claim 1, comprising (percentages by weight):

| | |
|---|---|
| oleoylethanolamide (OEA) C18:1 | 61-63% |
| palmitoylethanolamide (PEA) C16:0 | 17-19% |
| linoleylethanolamide (LEA) C18:2 | 5-5.7% |
| stearoylethanolamide (SEA) C18:0 | 1.2-1.7% |
| palmitoleoylethanolamide (POEA) C16:1 | 0.3-0.5% |
| myristoylethanolamide (MEA) C14:0 | 0.03-0.11% |
| mixture of glycerides | 5-5.5% |
| glycerol | 7-7.5%. |

3. The acylethanolamide composition according to claim 1, comprising (percentages by weight):

| | |
|---|---|
| oleoylethanolamide (OEA) C18:1 | 61-63% |
| palmitoylethanolamide (PEA) C16:0 | 7-12% |
| linoleylethanolamide (LEA) C18:2 | 8-15% |
| stearoylethanolamide (SEA) C18:0 | 1.2-1.7% |
| palmitoleoylethanolamide (POEA) C16:1 | 0.3-0.5% |
| myristoylethanolamide (MEA) C14:0 | 0.03-0.11% |
| mixture of glycerides | 5-5.5% |
| glycerol | 7-7.5%. |

4. A method of direct uncatalyzed aminolysis in the absence of solvent from olive oil with 2-aminoethanol, comprising the following steps:
  a) mixing olive oil with 2-aminoethanol;
  b) heating the mixture of step a) to a temperature between 120° C. and 160° C.;
  c) separating the acylethanolamide composition according to claim 1, obtained in the form of a waxy solid;
  d) optionally, absorbing the acylethanolamide composition of step c) on porous amorphous silica, thus obtaining an absorption compound of acylethanolamide complex and porous amorphous silica.

5. The method according to claim 4, wherein in step a) the weight ratio of olive oil/2-ethanolamine is between 100:13 and 100:22.

6. The method according to claim 4, wherein step b) is carried out at a temperature between 130° C. and 150° C., and for a time over 2 hours and less than 5 hours.

7. The method according to claim 4, wherein step d) is carried out by melting the acylethanolamide composition of step c) at a temperature between 70° C. and 90° C. and then adding porous amorphous silica, and wherein the weight ratio of acylethanolamide composition to porous amorphous silica is between 0.9:1 and 1.1:1.

8. An absorption compound of acylethanolamide complex and porous amorphous silica, comprising the acylethanolamide composition of claim 1.

9. A human or veterinary pharmaceutical formulation comprising the acylethanolamide composition according to claim 1 or an absorption compound of acylethanolamide complex and porous amorphous silica, comprising the acylethanolamide composition, wherein the formulation is in dosage forms for oral, buccal, parenteral, rectal, or transdermal administration.

10. The pharmaceutical formulation according to claim 9, wherein the acylethanolamide composition is contained in a liquid dosage form.

11. The pharmaceutical formulation according to claim 9, wherein the absorption compound of acylethanolamide complex and porous amorphous silica is contained in a solid dosage form.

12. A dietary formulation, food supplement or food for special medical purposes (FSMP), comprising the acylethanolamide composition according to claim 1 or an absorption compound of acylethanolamide complex and porous amorphous silica comprising the acylethanolamide composition.

13. A method for treating a low grade neuroinflammation comprising administering an effective amount of the acylethanolamide composition according to claim 1.

14. The method according to claim 13, wherein the method comprises treatment of a population of patients suffering from obesity.

15. The method according to claim 4, wherein in step a) the weight ratio of olive oil/2-ethanolamine is between 100:15 and 100:20.

16. The method according to claim 4, wherein in step a) the weight ratio of olive oil/2-ethanolamine is between 100:16 and 100:18.

17. The method according to claim 4, wherein step b) is carried out at a temperature between 135° C. and 145° C., and for a time over 2 hours and less than 5 hours.

18. The method according to claim 4, wherein step b) is carried out at a temperature between 130° C. and 150° C. for a time over 2 hours and less than 5 hours.

19. The method according to claim 4, wherein step d) is carried out by melting the acylethanolamide composition of step c) at a temperature between 70° C. and 90° ° C. and then adding porous amorphous silica, and wherein the weight ratio of acylethanolamide composition to porous amorphous silica is about 1:1.

* * * * *